United States Patent [19]
Crossley et al.

[11] Patent Number: 5,965,696
[45] Date of Patent: Oct. 12, 1999

[54] POTASSIUM CHANNEL MODULATORS

[75] Inventors: Roger Crossley, Woodley; Albert Opalko, Maidenhead; David Geraint Owen; Brian Robertson, both of London, all of United Kingdom

[73] Assignee: John Wyeth & Brother, Ltd., Maidenhead, United Kingdom

[21] Appl. No.: 08/451,371

[22] Filed: May 26, 1995

Related U.S. Application Data

[62] Division of application No. 08/233,610, Apr. 26, 1994, abandoned.

[51] Int. Cl.$^6$ .............................. A61K 38/00; C07K 5/00; C07K 7/00
[52] U.S. Cl. ............................................................ 530/324
[58] Field of Search ................................ 530/324; 514/12

[56] References Cited

U.S. PATENT DOCUMENTS 5,356,775  10/1994  Heber et al. ................................ 435/6

OTHER PUBLICATIONS

Rettig et al., *The Embo Journal,* vol. 11, No. 7, pp. 2473–2486, 1992.
Schröter et al., FEBS Letters, vol. 278, No. 2, pp. 211–216, Jan. 1991.
Aldrich, Science, 250, 568–571 (1990).
Ruppersberg et al., Nature, 353, 657–660 (1991).
Robertson B and Owen D., J. Physiol., 459, 92P (1993).
Rudy et al., J. Neuroscience Res., 29, 401–412 (1993).
Ruppersberg et al., Nature, 352, 711–714 (1991).

*Primary Examiner*—Avis M. Davenport
*Attorney, Agent, or Firm*—Arthur G. Seifert

[57] ABSTRACT

This invention concerns peptides (I) having intracellular potassium channel modulating activity comprising the amino acid sequence shown in SEQ ID No: 2:

```
(N terminal function)                          (I)

Met Ile Ser Ser Val Cys Val Ser Ser
1               5

Tyr Arg Gly Arg Lys Ser Gly Asn Lys
10                  15

Pro Pro Ser Lys Thr Cys Leu Lys Glu Glu
        20              25

(C terminal function)
``` in which the cysteines are optionally linked via a disulphide bridge and wherein > Met represents L-methionine
> Ile represents L-isoleucine
> Ser represents L-serine
> Val represents L-valine
> Cys represents L-cysteine
> Tyr represents L-tyrosine
> Arg represents L-arginine
> Gly represents glycine
> Lys represents L-lysine
> Asn represents L-asparagine
> Pro represents L-proline
> Thr represents L-threonine
> Leu represents L-leucine
> Glu represents L-glutamic acid or a variant thereof,
with the proviso that excluded is the 13-Lys variant (where 13-Arg is replaced by 13-Lys) in which the cysteines are not linked via a disulphide bridge, which are useful in a test method of screening for compounds having potassium channel modulating activity.

9 Claims, No Drawings

POTASSIUM CHANNEL MODULATORS

This is a division of application Ser. No. 08/233,610 filed Apr. 26, 1994 and now abandoned.

This invention relates to potassium channel modulators, in particular to linear and cyclic peptides which block potassium channels intracellularly and are useful in screening for potential potassium channel openers having therapeutic utility.

Voltage gated potassium ion (K+) channels which produce outward currents are present in the cell membranes of neurones and serve to repolarise the cell following a depolarisation by opening and allowing potassium ions to flow from the inside of the cell to the outside. They are, therefore, one of the main regulating influences on the nerve cell firing and determine the amount of current reaching the terminal regions of the cells. This in turn regulates the amount of neurotransmitter substances released from the nerve terminals. In addition, they help to determine the refractory period of the nerve cell and hence the probability of the cell firing again within a certain time. This governs neuronal excitability and also the tendency of a cell to undergo repetitive firing. An ability to modify the functioning of these channels by chemical means is the aim of current research in the search for therapeutically useful agents.

The present application is particularly concerned with the intracellular block of the K+ channels.

Voltage-dependent potassium (K+) channels open in response to a positive shift in membrane potential. After some variable time these channels close again; certain types of K+ channels close fairly quickly ("inactivate" in several milliseconds) after opening, others remain open for seconds. It was suggested over twenty years ago that the rapid closing mechanism is due to a 'molecular plug' or ball swinging into the open channel thereby blocking the further passage of ions. This simple mechanism has recently been shown to account for the rapid inactivation of several K channels. Initially Aldrich et al., Science 250 568–571 (1990), demonstrated that only 20 amino acids at the N terminal of Shaker B channels acts as the blocking particle. Similarly, Ruppersburg J P et al., Nature 353 657–660 (1991), have recently shown for some mammalian (rat) potassium channels (called Raw3 and RCK4) that the N-terminal regions act as the natural channel closing particle.

Robertson B., and Owen D., J. Physiol., 459, 92P, 1993 have also shown that non-inactivating K channels from a mammalian brain (MK-1) may be blocked by a peptide derived from the N-terminal sequence of the Shaker B channel. This has the overall effect of transforming this previously sustained channel into a rapidly inactivating one. Rudy, D., et al., J. Neuroscience Res., 29, 401–412 (1991), give the amino acid sequence for a human brain inactivating potassium channel (HKShIIIc), which is extremely homologous to the rat inactivating K channel Raw3.

All of the above known peptide sequences are understood to be 'linear' molecules in so far as there is no intramolecular chemical bonding. However physical intramolecular forces may give the molecule some degree of constraint.

A 28-amino acid peptide derived from the N-terminal sequence of HKShIIIc was synthesised ('human' 28 mer peptide) and tested in the non-activating MK-1 channel to determine if this isolated peptide was capable of blocking the channel. This 'human' 28 mer peptide had the sequence listed in SEQ ID No: 1:

```
Acetyl Nle Ile Ser Ser Val Cys Val Ser Ser Tyr Arg
       1               5                      10

Gly Arg Lys Ser Gly Asn Lys Pro Pro Ser Lys Thr
            15                      20

Cys Leu Lys Glu Glu NH2
  25
```

An acetyl group was used to block the terminal NH$_2$-group.

We have found that the 'human' 28 mer peptide was active in transforming MK-1 into an inactivating channel.

Most surprisingly we have found that the cyclic cysteine—cysteine bridged analogues were also active and apparently more potent than the 'linear' form as K+ channel blockers.

Accordingly this invention provides a peptide (I) having intracellular potassium channel blocking activity comprising the amino acid sequence listed in SEQ ID No: 2:

```
(N terminal function) Met Ile Ser Ser Val Cys    (I)
                      1                   5

Val Ser Ser Tyr Arg Gly Arg Lys Ser Gly Asn Lys
                10                      15

Pro Pro Ser Lys Thr Cys Leu Lys Glu Glu
        20                  25

(C terminal function)
``` in which the cysteines are optionally linked via a disulphide bridge and wherein > Met represents L-methionine
> Ile represents L-isoleucine
> Ser represents L-serine
> Val represents L-valine
> Cys represents L-cysteine
> Tyr represents L-tyrosine
> Arg represents L-arginine
> Gly represents glycine
> Lys represents L-lysine
> Asn represents L-asparagine
> Pro represents L-proline
> Thr represents L-threonine
> Leu represents L-leucine
> Glu represents L-glutamic acid or a variant of said polypeptide having intracellular potassium channel modulating activity with the proviso that excluded is the 13-Lys variant (where 13-Arg is replaced by 13-Lys) in which the cysteines are not linked via a disulphide bridge.

As an example of a variant mention is made of the 1-Nle (norleucine) analogue replacing 1-methionine. Similarly Glu residues may be replaced by aspartic acid (Asp), and Asn residue by Gln (L-glutamine). In addition Arg and Lys residues may be interchanged. The term variant means any analogue having one (or more) different amino acid residues providing that intracellular potassium channel modulating activity is retained. The term also covers omission or addition of amino acid residues where said intracellular activity is retained.

The α-terminal group may be NH$_2$ (i.e. the N-terminal function is H—) or a substituted amino group, e.g. mono- or di-alkyl amino or N-acyl such as N-alkanoyl, e.g. N-acetyl. The C-terminal group may be hydroxy (i.e. the peptide is an acid) or a derivative thereof, e.g. an ester function e.g. —O-alkyl, or an amide, e.g. —NH$_2$, —NHalkyl or —N(alkyl)$_2$.

As used herein 'acyl' refers to carbonyl groups such as alkyl-, aryl- or aralkyl-carbonyl, e.g. having 2 to 15 carbon atoms, e.g. 2 to 7 for alkyl, 7 to 11 for aryl and 8 to 12 carbon atoms for aralkyl.

Examples of 'alkyl' groups as used herein are straight or branched chain alkyl groups especially those having 1 to 6 carbon atoms e.g. methyl, ethyl, propyl, isopropyl and butyl. Examples of 'aryl' are those of 6 to 10 carbon atoms e.g. phenyl and naphthyl each optionally substituted. Examples of aralkyl are groups of 7 to 11 carbon atoms e.g. benzyl, phenethyl or naphthylmethyl each optionally substituted. The term 'optionally substituted' means optional substitution by groups or radicals commonly used in pharmaceutical chemistry, such as alkyl, alkoxy, hydroxy, halo, nitro, amino, alkylamino, acylamino, carboxy, alkoxycarbonyl, mercapto, haloalkyl and aminocarbonyl.

The term 'aryl' also includes 'heteroaryl', i.e aromatic mono- or bi-cyclic groups having 5 to 10 ring atoms, at least one of which is a heteroatom, e.g. oxygen, nitrogen or sulphur. Examples are furanyl, thienyl, pyrrolyl, pyridyl, quinolyl and isoquinolyl.

The peptides of this invention can be used with a potassium channel, e.g. the MK-1 channel to provide a useful screen for the development of novel drugs designed to interfere with the normal inactivation processes of potassium ion channels. Whole-cell recordings of MK-1 channels expressed in cell lines show the modification of MK-1 current into a rapidly inactivating current as the added peptide dialyses into the cell. Addition of test compound to the cell can be made from the extracellular or intracellular side to determine whether such molecules hinder the inactivation process, either by binding to the inactivation peptide itself, or its 'receptor' on the ion channel. Compounds which impede the inactivation of potassium ion channels result in more effective braking of cellular activity, and lead to a decrease in both cell excitability and neurotransmitter release, and are potentially useful in preventing epileptiform activity.

Accordingly this invention also provides a test method for screening a test compound for potassium channel modulating activity which comprises administering said test compound to a cell having a potassium channel, said cell containing a peptide of this invention, to determine whether the inactivation process is affected by said test compound.

The cyclic peptides of this invention are prepared by a process comprising oxidising a corresponding linear peptide to form the disulphide bridge. Oxidation may be conveniently carried out by air (or gaseous $O_2$) oxidation or by use of potassium ferricyanide.

The corresponding linear peptide precursor can itself be prepared by deprotecting a fully or partially proctected precursor or resin supported precursor as described hereinafter.

For example a fully or partially protected precursor peptide may be represented by the formula (II) shown in SEQ ID No: 3:

or a variant thereof,
where $X^1$ is hydrogen or an α-amino protecting group,
$R^1$ is an hydroxy protecting group for the side chain of Ser or Thr or hydrogen,
$R^2$ is a mercapto protecting group or hydrogen,
$R^3$ is an hydroxy protecting group for the side chain of Tyr or hydrogen,
$R^4$ is an guanyl protecting group for the side chain of Arg or hydrogen,
$R^5$ is an amino protecting group for the side chain of Lys or hydrogen,
$R^6$ is a carboxy protecting group for the side chain of Glu or hydrogen,
$X^2$ is OH, a carboxy protecting group or bond to a solid phase support, e.g. $X^2$=—O—$CH_2$[polystyrene resin support] where the latter group represents one of the many functional groups present in the polystyrene resin;
providing at least one protecting group is present when $X^2$ is OH.

When $R^2$ is hydrogen the abovementioned precursor peptide may be cyclised by oxidation (e.g. gaseous $O_2$) prior to removal of all protecting groups.

Protecting groups for the α-amino group ($X^1$) are illustrated by (1) acyl type protecting groups such as: formyl, trifluoroacetyl, phthalyl, p-toluenesulfonyl (tosyl), nitrophenylsulfenyl, etc;

(2) aromatic urethane type protecting groups such as benzyloxycarbonyl and substituted benzyloxycarbonyl such as p-chlorobenzyloxycarbonyl, p-nitrobenzyloxycarbonyl, (3) aliphatic urethane protecting groups such as tert-butyloxycarbonyl, diisopropylmethoxycarbonyl, isopropyloxycarbonyl, allyloxycarbonyl, 2,2,2-trichloroethoxycarbonyl, amyloxycarbonyl;

(4) cycloalkyl urethane type protecting groups illustrated by cyclopentyloxycarbonyl,adamantyloxycarbonyl, cyclohexyloxycarbonyl;

(5) thiourethane type protecting groups such as phenylthiocarbonyl;

(6) alkyl type protecting groups such as triphenylmethyl (trityl);

(7) trialkylsilane groups such as trimethylsilane.

The side chain nitrogen atoms of arginine, are protected by a group ($R^4$) which may be nitro, tosyl, benzyloxycarbonyl, adamantyloxycarbonyl or tert-butyloxycarbonyl, preferably the tosyl group.

Protection for the side chain amino group of lysine ($R^5$) may be by tosyl, t-amyloxycarbonyl, t-butyloxycarbonyl, diisopropyloxycarbonyl, benzyloxycarbonyl, halobenzyloxycarbonyl, nitrobenzyloxycarbonyl, and the like, the 2-chlorobenzyloxycarbonyl group being preferred. Protection for the hydroxyl group of tyrosine, threonine and serine ($R^1$, $R^3$) may be with acetyl, benzoyl, tert-butyl, benzyl. The benzyl group is preferred for this purpose.

$$X^1 \text{ Met Ile Ser}(R^1) \text{ Ser}(R^1) \text{ Val Cys}(R^2) \text{ Val Ser}(R^1) \text{ Ser}(R^1) \text{ Tyr}(R^3) \text{ Arg}(R^4) \quad \text{(II)}$$
$$1 \qquad\qquad\qquad 5 \qquad\qquad\qquad\qquad\qquad\qquad 10$$

$$\text{Gly Arg}(R^4) \text{ Lys}(R^5) \text{ Ser}(R^1) \text{ Gly Asn Lys}(R^5) \text{ Pro Pro Ser}(R^1) \text{ Lys}(R^5)$$
$$15 \qquad\qquad\qquad\qquad\qquad\qquad 20$$

$$\text{Thr}(R^1) \text{ Cys}(R^2) \text{ Leu Lys}(R^5) \text{ Glu}(R^6) \text{ Glu}(R^6) \text{ } X^2$$
$$25$$

The protecting group for the sulfydryl group of the cysteinyl amino acid residue ($R^2$) can be a group selected from benzyl; substituted benzyl wherein the substituent is at least one of methyl, methoxy, nitro, or halo (e.g. 3,4-dimethylbenzyl, p-methoxybenzyl, p-chlorobenzyl, p-nitrobenzyl, etc.); trityl, benzyloxycarbonyl, benzhydryl, p-methoxybenzyloxycarbonyl, benzylthiomethyl, ethylcarbamoyl, thioethyl, tetrahydropyranyl, acetamidomethyl, benzoyl, s-sulfonate salt, etc.; p-methoxybenzyl group being preferred.

The carboxy group of glutamic acid may be protected ($R^6$) by a benzyl or substituted benzyl group.

The corresponding linear protected peptide precursor may be prepared by known methods for building up an amino acid sequence as described in standard textbooks on peptide synthesis. For example solid phase methodology can be used where the peptide is bound to a polystyrene resin support or a benzhydrylamine resin support following techniques generally known in the art for building up amino acid sequences from an initial resin supported amino acid such as illustrated by Merrifield, JACS, 85 2149 (1963).

The resin support employed may be any suitable resin conventially employed in the art for the solid phase preparation of polypeptides, e.g. a copolymer of styrene and divinyl benzene in which the degree of crosslinking by the divinyl benzene is from 0.5 to 3%; which resin has been chloromethylated to provide sites for ester formation with the initially introduced protected amino acid. The projected C-terminal (amino protected) amino acid may be coupled to the chloromethylated resin according to the procedure of Gisin, Helv. Chim. Acta., 56 1476 (1973). Following the coupling of the first amino protected to the resin support, the amino protecing group may be removed by standard methods employing trifluoroacetic acid in methylene chloride, trifluoroacetic acid alone or HCl in dioxane. The deprotection may be carried out at a temperature between 0° C. and room temperature. After removal of the amino protecting group the remaining a-amino protected and, if necessary, side chain protected amino acids are coupled, seriatim, in the desired order to obtain the product. Alternatively, multiple amino acid groups may be coupled by the solution method prior to coupling with the resin supported amino acid sequence. The selection of an appropriate coupling reagent is within the skill of the art. Particularly suitable coupling reagents are N,N'-diisopropylcarbodiimide and N,N'-dicyclohexylcarbodiimide.

Each protected amino acid or amino acid sequence is introduced into the solid phase reactor in a two to six fold excess and the coupling is carried out in a medium of dimethylformamide: methylene chloride or in either dimethylformamide or methylene chloride alone. In cases where incomplete coupling occurs the coupling procedure is repeated before removal of the α-amino protecting group, prior to introduction of the next amino acid to the solid phase reactor. The success of the coupling reaction at each stage of the synthesis can be monitored by the ninhydrin reaction as described by E Kaiser et al., Analyt. Biochem., 34, 595 (1970).

The necessary α-amino protecting group employed for each amino acid introduced in the polypeptide is preferably tert-butyloxycarbonyl, although any such protecting group may be employed as long as it is not removed under coupling conditions and is readily removed selectively in relation to the other protecting groups present in the molecule under conditions which otherwise do not affect the formed molecule. Additional examples of such a-amino protecting groups from which selection may be made, after consideration of the rest of the polypeptide molecule, are trityl, phthalyl, tosyl, allyloxycarbonyl, cyclopentyloxycarbonyl, tert-amyloxycarbonyl, benzyloxycarbonyl and o- or p-nitrobenzyloxycarbonyl.

The criteria for selecting protecting groups for $R^1$–$R^6$ are:

(a) the protecting group must be stable to the reagent and under the reaction conditions selected for removing the a-amino protecting group at each step of the synthesis, (b) the protecting group must retain its protecting properties (i.e not be split off under coupling conditions), and (c) the protecting group must be readily removable upon conclusion of the polypeptide synthesis, under conditions that do not otherwise affect the polypeptide structure.

Standard methods of removing the protecting groups sequentially or simultaneously may be used.

They may be removed before, after of simultaneously with cleavage from the resin support when present. Preferably cleaving and deprotection are carried out at the same time e.g. using hydrogen fluoride and anisole, to obtain the fully deprotected linear peptide. If a protected cyclic precursor peptide is prepared then deprotection gives the final cyclic peptide (I).

Where a variant of the sequence above is desired to be prepared, the variant amino acid(s) protected if required is (are) incorporated at the appropriate stage(s) in the synthesis.

The C-terminal group obtained by cleaving a compound of formula II where $X^2$ is OCH[polystyrene resin support] using HF is the carboxy function, i.e $X^2$=COOH. Alternatively the peptide may be removed from the support by ammonolysis with ammonia to give a $CONH_2$ terminal group, or by reaction with an amine such as alkyl $NH_2$ to give a CONH alkyl group. Cleavage by transesterification gives an ester terminal group e.g. COOR where R is an organic radical, e.g. alkyl or aralkyl as illustrated hereinabove.

The terminal amino acid function if not already modified prior to coupling may be modified after coupling by appropriate reaction of the precursor peptide, e.g. acylation using for example an acyl halide.

The wet solution method for preparing the compounds of this invention comprises coupling the requisite amino acids protected, modified and/or activated as necessary in any order of succession to give the desired peptide sequence and thereafter, in any order, removing one or more protecting groups and oxidising if desired to give a disulphide bridge.

The coupling of the amino acids in the above mentioned process may be carried out by the standard methods used in peptide chemistry. Such methods are described in the literature for example in standard textbooks on peptide synthesis—see for example Schroder and Lubke, "The Peptides", Academic Press 1965 and Greenstein and Winitz, "Chemistry of the Amino Acids" Vol. 2, John Wiley and Sons Inc. 1961.

The following Example illustrates the invention:

EXAMPLE 1

SEQ ID No: 4:

Acetyl Nle Ile Ser Ser Val Cys Val Ser Ser Tyr Arg
      1                    5                      10

Gly Arg Lys Ser Gly Asn Lys Pro Pro Ser Lys Thr
              15                   20

Cys Leu Lys Glu Glu $NH_2$, 6 Cys 24 Cys disulphide
   25

The title compound was prepared by bubbling air through an aqueous solution of the corresponding linear form.

The linear form is prepared according to the processes described above using standard solid phase synthesis.

Analysis of title compound $^1$H NMR spectrum: (D$_2$O containing TMS as internal reference, 400 MHz) resonances at δ 0.9–1.1 ppm (27H 9×Me); 1.25 ppm (doublet 1Me); 1.3–2.5 ppm (complex multiplets); 2.9 ppm (multiplet 2H); 3.0–3.1 ppm (multiplet 12H); 3.2–3.3 ppm (multiplet 6H); 3.6–4.1 ppm (multiplet); 4.2–4.6 ppm (multiplet); 6.88 ppm (doublet 2H); 7.2 ppm (doublet 2H).

The terminal methionine residue of the 'human' 28 mer peptide was replaced by norleucine in the compound of Example 1 to produce a variant peptide without removing potassium channel activity as shown hereinafter.

The peptide described in Example 1 of this invention was tested for blocking activity on the MK-1 voltage-activated K+ channel; according to the following standard test procedure:

CHO cells stably transfected with cDNA for MK-1 (Dr B Tempel et. al University of Washington, Nature, 332, 837–839 (1988)) were maintained in tissue culture using standard procedures and media for this cell line. Cells were plated on 35 mm plastic dishes and used subsequently for electrophysiology within 3 days.

Currents were recorded using the whole-cell voltage-clamp configuration of the patch clamp technique, using an Axopatch 1C amplifier (Axon Instruments). Patch electrodes were manufactured from aluminosilicate glass tubing and heat polished prior to use. No electrode coating was necessary for whole-cell recording. Signal acquisition and analysis was performed using pClamp software (Axon Instruments). A p/4 subtraction procedure was used to remove leak and capacitive currents on line. A holding potential of −100 mV was routinely used.

Two main protocols were used in testing drugs. 1) Current-voltage (I–V) curves were collected, with incrementing steps of either 10 or 20 mV. Full I–V curves were obtained both in control and drug solutions. 2) A 'pharmacology' programme, which involved single voltage steps from −100 mV to +60 mV, applied and collected at 20s intervals. Compounds under investigation were applied via a 'U' tube rapid perfusion system to a small area of the recording chamber. Drug applications were always bracketed by control solutions to ensure reversibility. The recording chamber was continuously perfused at 3 ml.min$^{-1}$. Results are expressed as % of control peak current (at +60 mV). However, where drugs have a time dependent effect on MK-1, i.e acceleration of decay, results are also expressed as a % of total charge transferred within the duration of the voltage step.

The standard extracellular solution contained (in mM): NaCl 135, KCl 5, MgCl$_2$ 4, EGTA 1, HEPES 10 and glucose 25, set to pH 7.4 with NaOH. The intracellular (pipette) solution comprised: K aspartate/K gluconate 120, KCl 20, MgCl$_2$, MgATP 2, EGTA 10, HEPES 10, pH at 7.4 with NaOH. This solution was stored in 1 ml aliquots at −4° C., and filtered at 0.2 mm. The MK-1 current is a slowly rising, very slowly inactivating current, which may reach several nA in amplitude at +60 mV.

In the abovementioned test procedure the cyclic peptide of Example 1 was found to have an inactivation time constant of 78 ms±20 ms at 60 mV. This a measure of the blocking potency.

We claim:

1. A peptide (I) having intracellular potassium channel modulating activity and having a 28 amino acid sequence, as listed in SEQ ID No: 2, which is

```
(N terminal group)                              (I)

Met Ile Ser Ser Val Cys Val Ser
1               5

Tyr Arg Gly Arg Lys Ser Gly Asn Lys
10                  15

Pro Pro Ser Lys Thr Cys Leu Lys Glu Glu
        20                  25

(C terminal group)
``` in which the cysteines are optionally linked via a disulphide bridge and wherein Met represents L-methionine
Ile represents L-isoleucine
Ser represents L-serine
Val represents L-valine
Cys represents L-cysteine
Tyr represents L-tyrosine
Arg represents L-arginine
Gly represents glycine -continued Lys represents L-lysine
Asn represents L-asparagine
Pro represents L-proline
Thr represents L-threonine
Leu represents L-leucine
Glu represents L-glutamic acid
Nle represents L-norleucine
Gln represents L-glutamine, the N-terminal group is an amino or substituted amino group, and the C-terminal group is —OH or —OC$_1$–C$_6$alkyl or a —NH$_2$, —NHC$_1$–C$_6$alkyl or —N(C$_1$–C$_6$alkyl)$_2$,
  or a variant thereof in which, independently, 1-Met is replaced by 1-Nle, or Glu is replaced by Asp, or 17-Asn is replaced by 17-Gln, or one or more Arg or Lys residues are interchanged,
  with the proviso that excluded is the 13-Lys variant where 13-Arg is replaced by 13-Lys in which the cysteines are not linked via a disulphide bridge,
  and wherein a substituted amino group is a mono- or di-C$_1$–C$_6$alkylamino group or a C$_2$–C$_7$alkyl-, aryl-, aralkyl- or heteroaralkyl-carbonylamino group, in which aryl is phenyl or naphthyl and heteroaryl is an aromatic mono- or bi-cyclic group having 5 to 10 ring atoms, at least one of which is a heteroatom, selected from O, N or S, which may be optionally substituted with one or more C$_1$–C$_6$alkyl, C$_1$–C$_6$alkoxy, hydroxy, halo, nitro, amino, C$_1$–C$_6$alkylamino, acylamino, carboxy, C$_1$–C$_6$alkoxycarbonyl, mercapto, haloC$_1$–C$_6$alkyl and aminocarbonyl groups.

2. A peptide as claimed in claim 1 in which the N-terminal group is an amino group or a C$_2$–C$_7$alkyl-, aryl-, aralkyl- or heteroaralkyl-carbonylamino group which may be optionally substituted as defined in claim 1.

3. A peptide as claimed in claim 1 in which the N-terminal group is a C$_2$–C$_7$alkyl-, aryl-, aralkyl- or heteroaralkyl-carbonylamino group.

4. A peptide as claimed in claim 1 in which the C-terminal group is —OH or —OC$_1$–C$_6$alkyl or a —NH$_2$, —NHC$_1$–C$_6$alkyl.

5. A peptide as claimed in claim 4 in which C$_1$–C$_6$alkyl is methyl, ethyl, propyl, isopropyl or butyl.

6. A peptide as claimed in claim 3 in which heteroaryl is optionally substituted furanyl, thienyl, pyrrolyl, pyridyl, quinolyl or isoquinolyl.

7. A peptide as claimed in claim 1 having a disulfide bond between the cysteine amino acids.

8. A peptide as claimed in claim 1 which has the sequence as listed in SEQ ID No: 4, which is

```
Acetyl Nle Ile Ser Ser Val Cys Val Ser Ser Tyr Arg
       1             5                      10

Gly Arg Lys Ser Gly Asn Lys Pro Pro Ser Lys Thr
            15                  20

Cys Leu Lys Glu Glu NH2,
     25
``` wherein the Cys 6 and the Cys 24 form a disulphide bond.

9. A peptide as claimed in claim 1 which has the sequence as listed in SEQ ID No: 5 which is

```
Acetyl Nle Ile Ser Ser Val Cys Val Ser Ser Tyr Arg
       1             5                      10

Gly Arg Lys Ser Gly Asn Lys Pro Pro Ser Lys Thr
            15                  20

Cys Leu Lys Glu Glu NH2.
     25
```

* * * * *

SEQUENCE LISTING (1) GENERAL INFORMATION:

(iii) NUMBER OF SEQUENCES:  5

(2) INFORMATION FOR SEQ ID NO: 1:

(i) SEQUENCE CHARACTERISTICS:
      (A) LENGTH:  28 amino acids
      (B) TYPE:  amino acid
      (D) TOPOLOGY:  linear (ix) FEATURE:  The Xaa in position 1 is acetyl Nle
      (A) NAME/KEY:

(xi) SEQUENCE DESCRIPTION:SEQ  ID NO: 1:

Xaa Ile Ser Ser Val Cys Val Ser Ser Tyr Arg Gly Arg Lys
1               5                   10

Ser Gly Asn Lys Pro Pro Ser Lys Thr Cys Leu Lys Glu Glu
15              20                  25

(2) INFORMATION FOR SEQ ID NO: 2:

(i) SEQUENCE CHARACTERISTICS:
      (A) LENGTH:  28 amino acids
      (B) TYPE:  amino acid
      (D) TOPOLOGY:  both (ix) FEATURE:
      (A) NAME/KEY:

(xi) SEQUENCE DESCRIPTION:SEQ  ID NO: 2:

Met Ile Ser Ser Val Cys Val Ser Ser Tyr Arg Gly Arg Lys
1               5                   10

```
Ser Gly Asn Lys Pro Pro Ser Lys Thr Cys Leu Lys Glu Glu
15                  20                  25
```

(2) INFORMATION FOR SEQ ID NO: 3:

(i) SEQUENCE CHARACTERISTICS:
        (A) LENGTH: 28 amino acids
        (B) TYPE: amino acid
        (D) TOPOLOGY: both (ix) FEATURE:
        (A) NAME/KEY:

(xi) SEQUENCE DESCRIPTION:SEQ ID NO: 3:

```
Met Ile Ser Ser Val Cys Val Ser Ser Tyr Arg Gly Arg Lys
1               5                   10
Ser Gly Asn Lys Pro Pro Ser Lys Thr Cys Leu Lys Glu Glu
15                  20                  25
```

(2) INFORMATION FOR SEQ ID NO: 4:

(i) SEQUENCE CHARACTERISTICS:
        (A) LENGTH: 28 amino acids
        (B) TYPE: amino acid
        (D) TOPOLOGY: circular (ix) FEATURE: Xaa is in position 1 acetyl Nle
         6 Cys 24 Cys disulphide
        (A) NAME/KEY:

(xi) SEQUENCE DESCRIPTION:SEQ ID NO: 4:

```
Xaa Ile Ser Ser Val Cys Val Ser Ser Tyr Arg Gly Arg Lys
1               5                   10
Ser Gly Asn Lys Pro Pro Ser Lys Thr Cys Leu Lys Glu Glu
15                  20                  25
```

(2) INFORMATION FOR SEQ ID NO: 5:

(i) SEQUENCE CHARACTERISTICS:
        (A) LENGTH: 28 amino acids
        (B) TYPE: amino acid
        (D) TOPOLOGY: both (ix) FEATURE: Xaa in position 1 is acetyl Nle
        (A) NAME/KEY:

(xi) SEQUENCE DESCRIPTION:SEQ ID NO: 5:

```
Xaa Ile Ser Ser Val Cys Val Ser Ser Tyr Arg Gly Arg Lys
1               5                   10
Ser Gly Asn Lys Pro Pro Ser Lys Thr Cys Leu Lys Glu Glu
15                  20                  25
```